United States Patent [19]

Bloss

[11] Patent Number: 4,692,024
[45] Date of Patent: Sep. 8, 1987

[54] AUTOMATIC REFRACTOMETER
[75] Inventor: F. Donald Bloss, Blacksburg, Va.
[73] Assignee: Electro-tec Corporation, Blacksburg, Va.
[21] Appl. No.: 732,689
[22] Filed: May 10, 1985
[51] Int. Cl.[4] ............................................. G01N 21/41
[52] U.S. Cl. ..................................... 356/135; 356/128; 350/619
[58] Field of Search ............... 356/128, 131, 132, 135, 356/136; 350/619, 622, 623

[56] References Cited

U.S. PATENT DOCUMENTS

| | | | |
|---|---|---|---|
| 2,885,923 | 5/1959 | Simmons | 356/136 |
| 3,157,788 | 11/1969 | Roche | 356/136 |
| 3,695,631 | 2/1972 | Gupta | 356/136 |
| 4,021,102 | 5/1977 | Iizuka | 356/128 |

FOREIGN PATENT DOCUMENTS

| | | |
|---|---|---|
| 785563 | 10/1957 | United Kingdom . |
| 1271172 | 4/1972 | United Kingdom . |
| 2087554 | 5/1982 | United Kingdom . |

OTHER PUBLICATIONS

"Introduction to the Methods of Optical Crystallography"; Bloss, (1961); pp. 10 and 11.
"The Spindle Stage: Principles and Practice"; Bloss, (1981); pp. 180 to 187.
"Handbook of Gem Identification"; Liddicoat, Jr., (1951); pp. 24 to 33.
"Das Polarisationmikroskop"; Conrad Burri, (1950); pp. 229 and 230.
"Gemology"; Herlbut and Switzer, (1979); pp. 66 to 68.
"The Jeweler's Refractometer as a Mineralogical Tool"; American Mineralogist; Hurlbut, Jr., (1984); vol. 69; pp. 391 to 398.
"The Refractometer in Mineralogy Instruction"; McKaque; pp. 67 to 72.
A Compendium of "BS" Brochures Pertaining to a description of Abbe, Pocket, Immersion, Projection and Process Refractometers and Components used therewith such as a Process Transmitter, General Description of a Differential Refractometer, pp. 1 to 29.
"Geometrical and Physical Optics"; Longhurst, (1967); pp. 87 to 89.
"Fundamentals of Optics"; Jenkins and White, (1976); pp. 24 to 28.
"Lehrbuch der Kristalloptik"; Pockels, (1906); pp. 110 to 117 and 128 to 131.
"The Methods of Petrographic-Microscopic Research—Their Relative Accuracy and Range of Application"; Wright, (1911); pp. 98 to 100.
"Matrix Methods in Optical Instrument Design", Brouwer, (1964); pp. 239 to 243.
"Geological Society of America—Memoir 8—The Universal Stage (with Five Axes of Rotation)"; Emmons, (1928); pp. 55 to 103.
"The Spindle Stage—Principles and Practice"; Bloss, (1981); Preface, pp. ix to xii, pp. 1 to 5 and 193 to 226.
"Physical Methods in Modern Chemical Analysis"; vol. 2; Kuwana, (1980); pp. 337 to 400.

Primary Examiner—R. A. Rosenberger
Assistant Examiner—Crystal D. Cooper
Attorney, Agent, or Firm—Watson, Cole, Grindle & Watson

[57] ABSTRACT

An optical refractometer for automatically determining the principal indices of a specimen receives an incident radiation beam which is reflected by a first rotatable mirror onto a reflecting surface of a first elliptical mirror wherein the axis of rotation of the first rotatable surface extends through a first focus of the first elliptical mirror. A hemicylinder has a center of curvature at a second focus of the first elliptical mirror and rotatably and translatably mounts a specimen about a first axis and along second and third axes, respectively, such that a portion of the specimen is located at the second focus to receive the reflected incident beam from the first rotatable surface. A second elliptical mirror has third and fourth foci and a second surface for reflecting the incident radiation beam from the second elliptical mirror with an axis of rotation extending through the fourth focus with the third focus being at the first axis coincident with the second focus for producing a reflected beam output. The rotation of the first and second rotatable surface is controllable to alter the angle of the incident radiation and the angle of the reflected beam output, and for rotating the specimen about the first axis and translating it along the second and third axes.

42 Claims, 15 Drawing Figures

AUTOMATED REFRACTOMETER SYSTEM CONTROLS FLOW CHART

AUTOMATIC REFRACTOMETER

BACKGROUND OF THE INVENTION

The invention is directed to refractometer apparatus for measuring principal refractive indices of solids and liquids, and more particularly to the automation of such method and apparatus with expanded capabilities of automatically scanning a specimen and computing refractive indices with commensurate additional functions of differing phase indication, mapping thin sections and the plotting of petrofabric diagrams, etc.

Geologists, and particularly petrographers, devote much of their efforts studying thin sections of specimens to obtain goals such as the identification of various minerals present in thin sections of both rocks and ceramic materials and the estimation of the relative volumetric proportions of the minerals in the thin sections, and to determine the orientation of the optical indicatrix for all crystals of each mineral if it is anisotropic and non-opaque in the thin section in order to prepare a petrofabric diagram showing the preferred orientation, or lack thereof. There is a need to perform all such functions automatically in less time than now currently achievable. At present the determination of the orientation of the optical indicatrix for crystals and the petrofabric study of rocks is so time-consuming for optically biaxial crystals that it is rarely attempted by petrographers.

The routine techniques of optical crystallography have remained substantially stagnant subsequent to the development of the double-variation method by Emmons in 1928. In contradistinction thereto, X-ray crystallography has been revolutionized by the use of high speed computers, sophisticated statistical methods, and automation and thus has flourished as opposed to the atrophy of optical crystallography. From the use of carefully adjusted Abbe-Pulfrich refractometers, researchers have been able to measure, with a precision of 0.0002, the three principal refractive indices of biaxial crystals ($\alpha$, $\beta$ and $\gamma$). However, in this century mineralogists have gradually abandoned such techniques because they required a flat surface of appreciable area to be cut and polished on a crystal specimen. Therefore oil immersion techniques became increasingly popular because they were applicable to small, irregularly-shaped grains. Fortunately, gemologists retained the use of the refractometer which was ideal for non-destructive tests on cut and polished gems.

With the increasing popularity of the immersion method, a precision of routine refractive index measurements of + or −0.002 or + or −0.003 became acceptable although better precision was still achievable with double-variation methods. The general acceptance of such poor precision caused optical crystallography to lose effectiveness as a research tool in mineralogy.

More recent studies using spindle stage methods have disclosed that in research on mineral series wherein solid solution and/or order-disorder are involved, optical crystallography can be a powerful ally of X-ray crystallography. Such studies have produced the following advantages: (1) all principal indices and the dispersion of each were directly measurable from a single grain with a precision better than 0.0005; (2) the optical angle 2V of biaxial crystals was determinable, generally within a fraction of a degree, by the use of Bloss and Riess techniques and the computer program EXCALIBR (Bloss 1981); (3) the same crystal could then be studied by X-ray methods; and (4) the same crystal could be analyzed by electron microprobe.

The operative part of a jeweler's refractometer is a glass hemicylinder having a refractive index generally greater than 1.8 which sets the upper limit of the indices that are measurable. For convenience of reference, three rectangular Cartesian axes x, y and z will be defined herein such that x and y lie within the hemicylinder's polished plane with y coinciding with the axis of the cylindrical surface. An isotropic solid is placed with its cut and polished plane against the hemicylinder's xy plane and, to promote optical contact and adherence between the two planes, between them is placed a droplet of oil having a refractive index less than the hemicylinder but exceeding that of the refractive index of the solid. A cross-section through the solid specimen and the hemicylinder will show the critical angle phenomena that for a monochromatic light source permit the solid's refractive index, through measurement of the critical angle, to be determined. As is known, the image of the light-dark boundary is passed through a transparent scale and, after reflection by a mirror, is observed through a suitable lens system. The transparent scale can be calibrated to yield either the solid's refractive index for sodium light or its critical angle in fractions of a degree.

In the measurement of an anisotropic crystal, unless a polarizer is introduced into the light path, the single light-dark boundary associated with an isotropic solid will be replaced by two boundaries, namely a boundary between a light and not-so-light area as well as one between a not-so-light and a dark area. When in contact with the hemicylinder's xy plane, an anisotropic crystal, whether uniaxial or biaxial, exhibits two refractive indices which are not necessarily the principle indices. Their significance becomes apparent if it is considered that for an angle of incidence infinitessimally less than the critical angle, the refracted wave front travels within the crystal along a direction that practically coincides with the +x Cartesian axis. It is known that the two light vibrations associable with this wave front lie within this wave front and coincide with the major and minor axes of the ellipse formed by the intersection between the crystal's optical indicatrix and this wave front, which practically coincides with the yz plane. If it is assumed that the crystal is biaxial, its optical indicatrix possesses three mutually perpendicular, principal axes usually labelled X, Y and Z. If light vibrates parallel to X in the crystal, the crystal exhibits its smallest principal refractive index $\alpha$; if parallel to Z it exhibits its largest principal refractive index $\gamma$; and if parallel to Y it exhibits the intermediate principal index $\beta$.

SUMMARY OF THE INVENTION

The method and apparatus of the present invention automatically measures the principal refractive index (n) for an isotropic solid or liquid. For anisotropic materials it will measure their two principal refractive indices $\epsilon$ and $\omega$ if uniaxial, and their three principal refractive indices $\alpha$, $\beta$ and $\gamma$ if biaxial. Concurrently for anisotropic materials, it will determine relative to its rectangular Cartesian axes the stereographic coordinates and thus the orientation (1) of the c crystallographic axis for uniaxial materials and (2) of the three principal vibration axes X, Y and Z for biaxial materials. The refractive method and apparatus of the present invention can perform the above functions beyond, as well as within, the visible electromagnetic range depending upon the spectral output of the light source and the spectral response or sensitivity of the sensor photomultiplier (or other device capable of sensing electromagnetic radiation).

Applied to thin (customarily, but not necessarily, 0.03 mm thick) sections of rock, ceramic materials, and other synthetic or natural materials, the method and apparatus of the present invention will perform the above-mentioned measurements at each point of a user-selected x, y grid on the thin section. An associated computer will analyze the resultant data and provide, upon completion of the entire automated scan of the specimen, the following:

(1) The percentage of x,y points at which it encounters phase A, phase B, phase C . . . etc., these phases being differentiated, one from the other, by their differing refractive indices. Therefore all crystals of phase A would have the same principal refractive indices for the wavelength of "light" used. A "point count" thus results and provides an estimate of the volume percentages of each solid phase composing the rock, ceramic or other material being investigated.

(2) The computer will print an enlarged map of the thin section that shows grain shapes and indicates whether each grain shape represents phase A, B, C, etc. For anisotropic grains for each shape it will print, as desired, the principal or the non-principal orientation-controlled refractive indices. The refractive method of the invention will distinguish neighboring grains of, for example, phase A, by differing orientation of the grains.

(3) For each anisotropic phase A, B, C, etc., the computer will plot a petrofabric diagram on a stereonet (=Wulff net) or on a Schmidt net. Such plots, especially for biaxial crystals, have heretofore demanded many hours of a structural petrologist's time. When ceramic parts fail, such petrofabric diagrams may possibly provide an answer.

(4) Functions (1), (2) and (3) can be performed for UV or IR wavelengths. Thus, thin sections of coal, although mostly opaque within the visible range, may be newly studied using the method and apparatus of the present invention.

(5) The method and apparatus of the present invention, equipped with a sample holder that permits flow-through of liquids (and control or measurement of their temperature), has potential use for industries in the quality control of liquids that are used or produced therein. The computer associated with the method and apparatus of the present invention could convert the refractive index it measures to a digital display of the percent sugar or total dissolved solids in fruit syrups, beverage concentrates, jams, jellies, or juices from beets, sugar cane or citrus fruits. Alternatively, the conversion could be to percent of alcohol in beer, wine or other fermented liquids prior to their bottling or storage in casks.

The petroleum industry represents an even larger potential market for the flow-through liquid measuring method and apparatus of the present invention since refractive indices provide information about the nature of hydrocarbon mixtures. Thus, low refractive indices are associated with paraffins, whereas aromatic hydrocarbons have higher indices. Hence, compositional changes in one or more of the petroleum fractions produced during the course of a process (distillation, extraction, crystallization, etc.) could be easily and continuously detected and monitored by the method and apparatus of the present invention.

The method and apparatus of the present invention could be equipped to set off warning bells and/or alarms and/or lights if the refractive index of a flow-through liquid varied outside of acceptable tolerances.

Particularly in the petroleum and coal industries, the potential of the method and apparatus of the present invention for measuring refractice indices for IR and/or UV wavelengths may become important.

The method and apparatus of the present invention have the following advantages:

(1) The very finely collimated entrance beam that it uses permits measurement of the refractive index at a relatively fine point on the surface of a smoothly polished solid.

(2) The frequency or wavelength of the electromagnetic radiation composing the entrance beam can be readily changed to permit direct measurement of refractive indices beyond, as well as within, the visible range by the very nature of the photo-detector determination of the critical angle.

(3) The automated x,y translation and z rotation of the refractive method and apparatus permit it to determine for an uncovered, polished thin section of rock, ceramic or plastic material: (a) all principal indices of the material at each point and, for anisotropic crystals, their orientation-controlled index; and if anisotropic, (b) the orientation of the crystallographic c axis for uniaxial crystals or of the principal vibration axes X, Y and Z for biaxial crystals.

(4) The computer software of the refractive method and apparatus will: (a) plot an enlarged map of the grain shapes for the thin section scanned; (b) plot a petrofabric diagram showing the preferred orientation, or lack thereof, for each different mineral or crystal phase present in the thin section; (c) compute the average cross-sectional grain size for each of these different phases; (d) estimate the percentage by volume of each crystal phase present in the rock or other specimen; (e) plot for each phase a statistical histogram showing the relative frequencies, according to specified classes of size, of the various cross-sectional areas of its grains; and (f) plot for each phase a "rose diagram" illustrating any preferred dimensional elongation for its grain cross-sections in the plane of the thin sections.

(5) Even if the point on which the automated refractometer's finely collimated incident beam impinges consists of several differently oriented crystals of the same mineral or crystal phase, the method and apparatus of the present invention will be able to measure the principal refractive indices. A rapid rotation of the sample about Cartesian axis z would aid in that determination. This feature should add impetus to studies of the optical properties of clays and other materials normally too fine-grained to permit optical studies.

(6) In simplified form wherein a flow-through liquid sample holder has replaced the x,y translatable, z rotatable sample holder, it can be used to monitor changes in the refractive index of a liquid being used or produced in a commercial process. In such a case it would be in competition with the Bellingham and Stanley model R.23E or RFM81 Automatic Refractometer. However the ability to measure at wavelengths beyond the visible range confers on the present invention an advantage. The method and apparatus could convert, at the touch of a button, from a digital display of refractive index to sugar (or alcohol) percent. A laminated hemicylinder would permit the method and apparatus of the present invention to equate to three (or more) B&S refractometers, each with a different prism.

(7) The method and apparatus of the present invention can measure very high refractive indices that are normally not measurable with precision and accuracy using the present routine methods.

(8) The determination of the orientations of anisotropic crystals, particularly biaxial ones, will render obsolete the expensive, laborious, skilled-operator-requiring Universal Stage methods.

(9) The method and apparatus of the present invention will permit operation by unskilled personnel and, moreover, will operate unattended.

(10) Ultimately, the method and apparatus of the present invention will permit routine measurement, for the first time, of refractive indices at wavelengths far outside the visible range. In doing so, it may disclose new areas for research. This feature plus the feature (9) will foster use in forensics and organic chemistry. Thus, forensic scientists measure the refractive indices and composition of the broken glass at the scene of a hit-and-run accident to limit the search to certain years, makes, and models of cars. The knowledge of refractive indices beyond the visible may further limit the search. In coal research, apparatus of the present invention, equipped with an IR laser source, may permit computer-enlarged maps of coal thin sections, which are normally opaque in visible light. Small refractive index differences may thus permit imaging of ancient pollen or other fossils.

(11) Optical mineralogy will, of course, be revolutionized. Immersion oils will no longer be needed to measure the refractive indices of minerals. This will eliminate the major source of error in refractive-index determinations, namely imprecise knowledge of the immersion oil's refractive index and temperature at the time of match between grain and oil.

BRIEF DESCRIPTION OF THE DRAWINGS

The above objects, features and advantages of the method and apparatus of the present invention will be more readily apparrent from the following description of preferred embodiments of the best mode of carrying out the invention when taken in conjunction with the following drawings wherein.

DETAILED DESCRIPTION

Figure 1A:
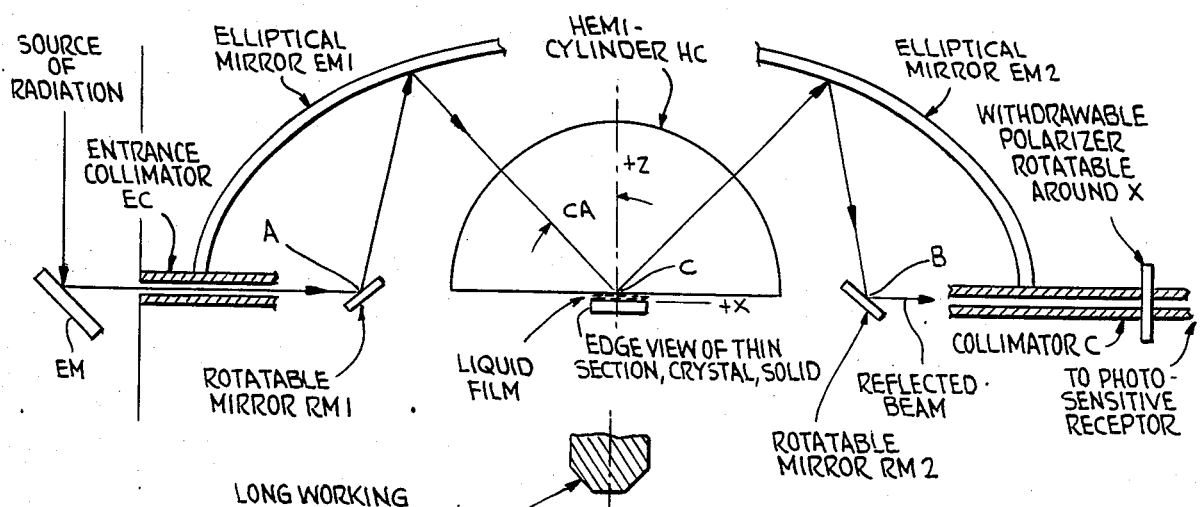
FIGS. 1A and 1B illustrate schematic cross-sections (perpendicular to Cartesian axis y) for two alternative embodiments of the automatic refractometer of the invention.
Figure 1B:
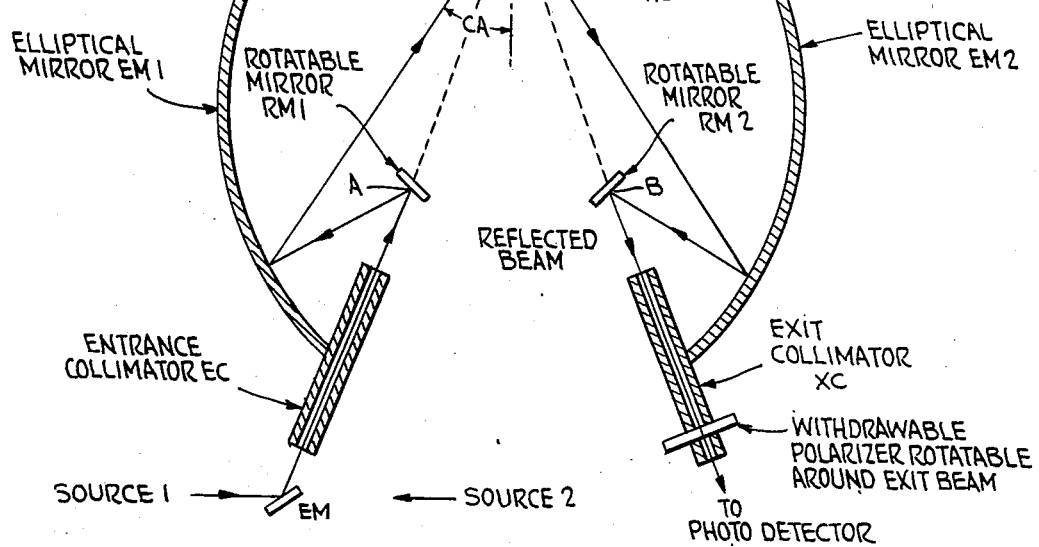

With respect to the schematic cross-sections through the refractometer portion of the automatic refractometer shown in FIGS. 1A and 1B, EM represents a first-surface mirror, rotatable on an axis (dashed) parallel to the z axis so that radiation from alternative sources (not shown) can be directed into the entrance collimator EC. In FIG. 1A line ACB coincides with the major axis of elliptical mirror 1 (EM1) and of elliptical mirror 2 (EM2). The two foci of EM1 are at A and C; those of EM2 are at C and B. Such collinearity of these two major axes is, however, not at all necessary. Preferable, indeed, is a more compact, alternative configuration wherein, as FIG. 1B shows, dotted line AC, which joins the two foci of EM1, is at an appreciable angle to line CB, which joins the foci of EM2. The angle between lines AB and CB may be chosen so as to optimize compactness and/or sensitivity of the refractometer. In addition, elliptical mirrors EM1 and EM2 may differ from each other in respect to the lengths of their major and minor axes. Hemicylinder HC, preferably made from cubic zirconia (n=2.15–2.18), has its center of curvature at C. The polished underface of hemicylinder HC, which is perpendicular to the page and passes through C, is in optical contact with the thin section at the specimen's polished upper surface by means of a thin film of liquid whose refractive index must exceed that of the specimen, but be less than that of the hemicylinder HC, as is known to the art. The two planar rotatable mirrors RM1 and RM2 rotate about an axis perpendicular to the plane of FIGS. 1A and 1B at points A and B. For simplicity, the x-and-y translatable, and z rotatable sample holder is not shown. The specimen is shown as an edge view.

More specifically, the two concave first surface elliptical mirrors EM1 and EM2 are mounted so that their major and minor axes are coplanar and such that one of the two foci of elliptical mirror EM1 precisely coincides with one of the two foci of elliptical mirror EM2. Transparent hemicylinder HC, having rectangular Cartesian axes x, y and z as shown in FIG. 1, is mounted with its Cartesian origin (0, 0, 0) precisely coincident with point C, the point where the foci of elliptical mirrors EM1 and EM2 coincide. FIG. 1A shows the angle between the major axes of EM1 and EM2 to equal zero degrees (or 180 degrees), but that condition is not a necessary one for operation of the automated refractometer of the invention. The two planar first-surface mirrors RM1 and RM2 are each rotatable on an axis parallel to the y axis of hemicylinder HC. The rotational axis of rotatable mirror RM1 passes through point A, a focus of elliptical mirror EM1; the rotational axis of planar mirror RM2 passes through point B, a focus of elliptical mirror EM2. Preferably stepper motors (not shown) will systematically rotate planar mirrors RM1 and RM2 under control of a computer (described hereinafter), such that at all times, rotatable mirrors RM1 and RM2 maintain an equal but opposite angle relative to the polished surface of hemicylinder HC. A less desirable alternative would be to have rotatable planar mirror RM1 to be rapidly rotated with only rotatable planar mirror RM2 being systematically rotated by a stepper motor.

A highly polished surface of the specimen whose refractive index is to be measured is placed in optical contact with the polished xy plane of hemicylinder HC. As is known to the art, such optical contact between the polished surface of hemicylinder HC and that of the specimen will be maintained by a thin intercalated film of a liquid having a refractive index exceeding that of the specimen, but less than that of hemicylinder HC. A finely collimated beam of highly monochromatic light, from for example a laser beam, enters the light proof chamber (not shown) through entrance collimator EC built into an appropriate aperture in elliptical mirror EM1. Radiation from the source strikes rotatable planar mirror RM1 which reflects the beam of radiation onto the surface of elliptical mirror EM1, which in turn reflects the light beam directly toward point C so that the radiation "light" beam enters hemicylinder HC by normal incidence. If rotatable planar mirror RM1 is set so that this finely collimated radiation beam impinges on plane xy at an angle that exceeds the critical angle CA between the hemicylinder HC and that of the specimen, the radiation beam will be totally reflected and will exit from hemicylinder HC to strike elliptical mirror EM2, which in turn reflects the radiation beam onto rotatable planar mirror RM2. Planar mirror RM2 reflects this beam into exit collamator XC and thus onto a photometric detector (not shown).

The directions along which the incident radiation beam enters the refractometer to strike RM1 and along which it exits from the refractometer after its reflection by RM2 may be altered to maximize compactness and sensitivity of the refractometer. In FIG. 1A they are shown to coincide with line ACB. Preferable, however, would be their entry and exit along directions like those shown in FIG. 1B. Indeed these directions of "light" entry and exit can be chosen so as to minimize or eliminate any obstruction of the beam paths by mirrors RM1 and RM2 themselves. Or to insure that, if they obstruct, it will be only for ray paths representative of critical angles corresponding to refractive indices that fall below the desired measuring range for the refractometer.

By adjusting rotatable planar mirrors RM1 and RM2 while paying proper attention to the response of the photometric detector to the light entering it, the critical angle CA of the specimen can be determined, and thereby the refractive index of the specimen for the wavelength of the light being used can be measured. A significant advantage of the photometric determination of the critical angle of the specimen is that the refractive indices of materials will become directly measurable not only for various visible wavelengths or frequencies but also for ultraviolet and infrared frequencies. The only requirements will be (1) a source of such frequencies, (2) their transmission by the hemicylinder which can be made of diamond to enhance that capability, and (3) a detector responsive to non-visible frequencies or wavelengths. Possible monochromatic sources of visible and non-visible frequencies usable with the automated method and apparatus of this invention include ordinary lasers, tunable lasers, as well as non-laser sources. A rotatable entrance mirror EM immediately outside of entrance collimator EC would permit several sources to be easily alternated for use with the automated refractometer. By rotation of mirror EM, a beam from one or the other of the aforementioned radiation sources could be caused to enter entrance collimator EC.

Two stepper motors (not shown) translate the specimen holder along Cartesian axes x and y and another stepper motor will rotate the specimen holder around axis z (relative to hemicylinder HC shown in FIG. 1. By means of computer-actuated translations along axes x and y, different points on the specimen's surface are successively centered on the BAR. The BAR then pauses to measure the specimen's refractive indices at this point before translating the specimen to the next x,y point of call. Thus the refractive indices of the specimen can be measured at each of a grid or rectangular network of points on the polished xy plane of the specimen. If desired, this could be accomplished for a variety of wavelengths within and beyond the visible spectrum. The dispersion of the specimen's refractive indices can thus be determined for each x, y point on such a rectangular grid. The computer will then print out a highly enlarged map of these x, y points showing, at each point, the specimen's measured refractive index for each wavelength. Thus, the variation in the refractive index in the cross-section of an optical fiber could be investigated.

The specimen holder of the automated refractometer will accommodate a petrographic thin section having a highly polished uncovered upper surface held in optical contact with the highly polished xy surface of the hemicylinder HC by a liquid having a refractive index less than that of the hemicylinder, but greater than that of the refractive index of any specimen in the thin section. The operator would determine the intervals of translation along the x and y axes, making such intervals small to investigate a relatively fine x, y grid of points if the thin-sectioned specimen consisted of a very fine-grained rock, for example. A coarser x, y grid would be satisfactory if the specimen were coarser-grained.

Most of the crystals in the petrographic thin section will likely be anisotropic rather than isotropic. In such a case the crystal will possess more than one principal refractive index for a given wavelength of radiation. For such a wavelength, optically uniaxial crystals possess two principal refractive indices, respectively symbolized $\epsilon$ for light vibrating parallel to their c crystallographic axis, and $\omega$ for light vibrating perpendicular to the c axis. For all other vibration directions they exhibit an index $\epsilon'$ which is intermediate between the $\epsilon$ and $\omega$ axes in value. Optically biaxial crystals possess three principal refractive indices, namely (1) $\alpha$, their smallest possible index for the given wavelength; (2) $\beta$, their intermediate index; and (3) $\gamma$, their largest possible index. Biaxial crystals exhibit these principal indices for light vibrating parallel to one of their three mutually perpendicular principal vibration axes X ($\alpha$), Y ($\beta$), and Z ($\gamma$). For light vibrating in a direction not coinciding with X, Y or X (or with a circular section of its optical indicatrix), a biaxial crystal will exhibit the refractive index $\alpha'$ or $\gamma'$ where $\alpha < \alpha' < \beta < \gamma' < \gamma$.

Figure 2:
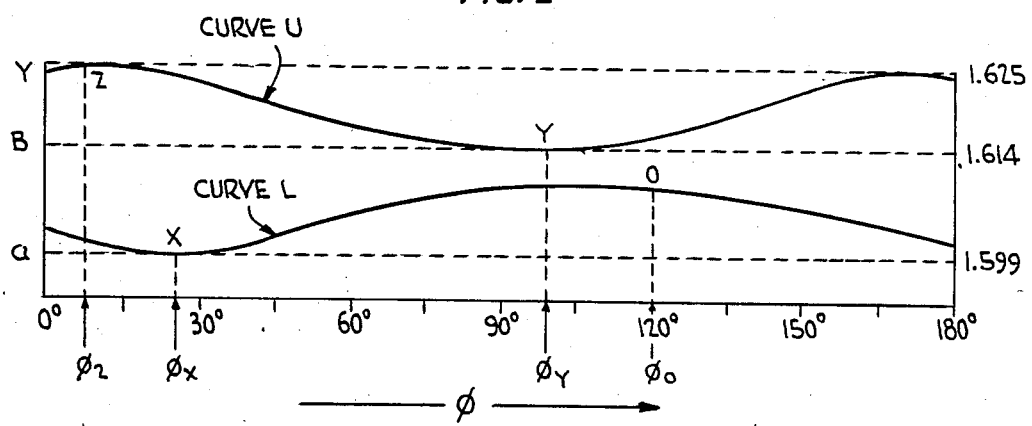
FIG. 2 is a plot of measured indices vs angle $\phi$, where $\phi$ represents the angle of rotation of the crystal or thin section about z, the direction perpendicular to its polished plane.

To determine the principal refractive indices of an anisotropic crystal, the automated refractometer, after stopping at an x, y point on the thin section of the specimen, will rotate the thin section about the z axis through an angle $\phi$ relative to the Cartesian axis x. Thus, the specimen holder's initial or non-rotated position will be at φ=0 degrees. For each new value of φ, as φ is varied from 0 degrees to 180 degrees by five degree or ten degree increments (or by any other suitable increment), the rotation about the z axis will pause until stepper-actuated rotatable mirrors RM1 and RM2 determine the crystal's critical angles, and thus its refractive indices for that particular value of φ. For each φ position if the crystal is anisotropic, two refractive indices will be measurable. Taking the more general case of a biaxial crystal, these two indices will be α' and γ' unless the particular value φ has brought a principal vibration axis X, Y or Z into the zy plane of hemicylinder HC. In this latter case, one measured refractive index will be α (if X lies in the zy plane), β (Y in the zy plane), or γ (Z in the zy plane). A plot of the variation of the measured refractive indices relative to φ would produce an upper curve U (as shown in FIG. 2) and a lower curve L. The maximum on curve U represents principal index γ, whereas the minimum point on curve L represents the principal index α. The φ values corresponding to the maximum (=γ) on curve U and the minimum (=α) on curve L are here symbolized as $\phi_Z$ and $\phi_X$ because they respectively represent φ values that orient Z and X into the hemicylinder's yz plane. Principal index β corresponds to either the minimum on curve U or the maximum on curve L. In FIG. 2 it is shown to have corresponded to the minimum on curve U; in such a case the corresponding φ value, symbolized $\phi_Y$, would have oriented Y into the hemicylinder's yz plane. The remaining extremum, labelled 0 in FIG. 2, represents a refractive index approximately equal to 1.607, corresponding to that radius of the optical indicatrix which happened to be precisely parallel to rotation axis z. "0" thus represents an orientation-controlled refractive index whose value will change with a change in the crystal's optical orientation relative to polished surface xy. For example, if the curves shown in FIG. 2 were compiled for several differently oriented crystals of precisely the same material, the three extrema γ=1.625, β=1.614 and α=1.599 would be repeated on curves U and L, but the orientation-controlled extremum "0" would change in value from 1.607 to other values. For differently oriented crystal specimens, the values of $\phi_X$, $\phi_Y$ and $\phi_Z$ would also differ from their values of 25 degrees, 99 degrees and 8 degrees in FIG. 2. If more precise values of $\phi_X$, $\phi_Y$ and $\phi_Z$ are desired, the automated refractometer would be controlled to scan across these preliminary values at, for example, one degree intervals. In other words, it would measure the minimum refractive index as φ was changed from 21 degrees to 22 degrees to 23 degrees . . . to 28 degrees, to determine a more precise value of $\phi_X$ and thus of index α. If even better precision in measuring α is desired, the sample should be rotated about z to $\phi_X$+180 degrees so that the index α could be redetermined. The average of these two values of α should be superior to either individual value.

Figure 3:
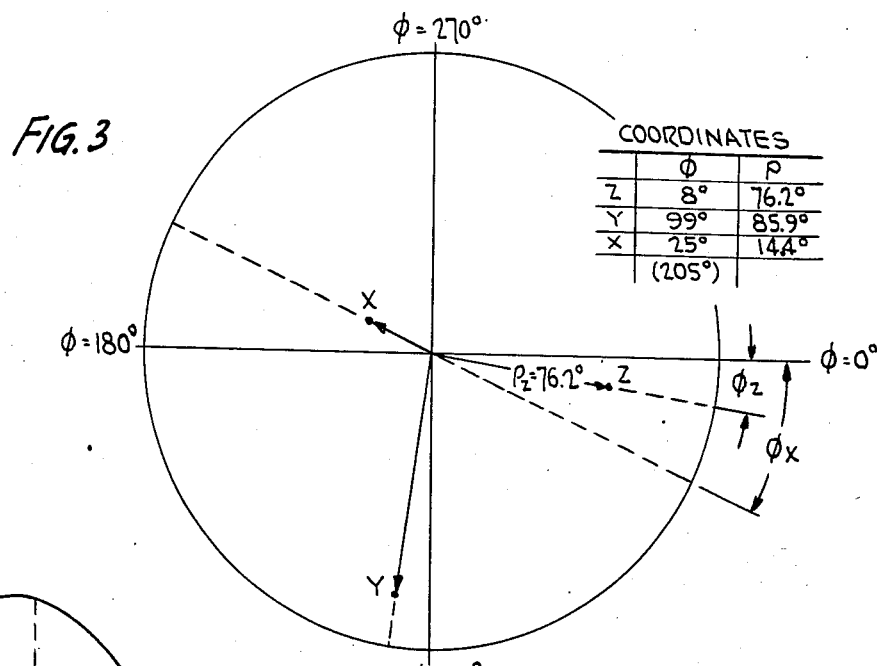
FIG. 3 illustrates a stereographic plot of a crystal's principal vibration axes in accordance with the invention.

A remarkable feature of the automated refractometer according to the invention is its ability to determine the orientation of a biaxial crystal's principal vibration axes X, Y and Z relative to the Cartesian axes, x, y and z of the refractometer. Thus, using the standard φ and ρ spherical coordinates described by Bloss (1971), Cartesian axis x could be plotted at φ=0 degrees, ρ=90 degrees, y at φ=90 degrees, ρ=90 degrees; and z at ρ=0 degrees as shown in FIG. 3. From the automated refractometer-compiled curves such as those illustrated in FIG. 2, the coordinates of X, Y and Z are known—thus $\phi_X$=25 degrees, $\phi_Y$=99 degrees and $\phi_Z$=8 degrees. The ρ angles X, Y and Z can now be directly determined by the automated refractometer's rotatable polarizer as discussed hereinafter.

With continuing reference to FIG. 2, for a randomly oriented biaxial crystal specimen whose polished surface is in optical contact with the highly polished xy surface of the hemicylinder HC, two refractive indices are always measurable while this crystal is being rotated around axis z, so that its φ angle is changed from 0 degrees to 180 degrees. A plot of the measured indices versus φ hence produces an upper curve U and a lower curve L, as has been previously described. The maximum on curve U and the minimum on curve L respectively represent refractive indices γ and α. Of the remaining two extrema, one corresponds to the principal refractive index β, whereas the other extremum corresponds to a non-principal orientation-dependent index labelled "0." For the same crystal specimen, if differently oriented relative to the xy surface of the automated refractometer, curves like those illustrated would indicate the same values for principal indices α, β and γ, whereas the orientation-oriented index "0" would differ from its value of 1.607. Thus, after measuring a second crystal specimen, the automated refractometer will "know" which extremum corresponds to β and which extremum corresponds to "0".

The φ values corresponding to the four extrema, namely $\phi_Z$ (approximately 8 degrees), $\phi_X$ (approximately 25 degrees), $\phi_Y$ (approximately 99 degrees) and $\phi_O$ (120 degrees) represent the values that respectively oriented Z, X and Y and the vibration corresponding to 0 into the automated refractometer's yz plane.

The angles between Cartesian axis z and Z, X, Y and O—symbolized $\rho_Z$, $\rho_X$, $\rho_Y$ and $\rho_O$—are directly determinable by inserting the automated refractometer's withdrawable, rotatable polarizer into the path of the exit beam. With φ set at $\phi_Z$, at $\phi_X$, at $\phi_Y$, and lastly at $\phi_O$, this polarizer is rotated until the critical angle corresponding to indices γ, α, β and "0" is no longer recognizable. The rotation of the polarizer's privileged direction relative to Cartesian axis z will then equal $\rho_Z$, $\rho_X$, $\rho_Y$ or $\rho_O$ or their complements, as desired. Because "0" coincides with z, $\rho_O$ will always equal zero degrees, whereas $\rho_Y$ will not. Hence, the extrema corresponding to "0" and β can be easily distinguished.

Alternatively, $\phi_X$, $\phi_Y$ and $\phi_Z$ can be calculated from spherical trigonometry by use of the following formulae:

$$\tan^2 \rho_X = - \frac{\cos(\phi_Z - \phi_Y)}{\{\cos(\phi_Y - \phi_X)\}\{\cos(\phi_Z - \phi_Y)\}}$$

$$\tan^2 \rho_Y = - \frac{\cos(\phi_Z - \phi_X)}{\{\cos(\phi_Y - \phi_Z)\}\{\cos(\phi_X - \phi_Y)\}}$$

$$\tan^2 \rho_Z = - \frac{\cos(\phi_Y - \phi_X)}{\{\cos(\phi_Z - \phi_X)\}\{\cos(\phi_Y - \phi_Z)\}}$$

The angles ($\phi_Z-\phi_X$), ($\phi_Y-\phi_Z$), and ($\phi_Y-\phi_X$) must each exceed or equal 90°. For the φ values observed from FIG. 2, this becomes true only if $\phi_X$ is increased by 180° to become 205°. This manipulation is valid because each of the extrema in FIG. 2 would also occur at their observed φ value plus 180°. FIG. 3 illustrates these calculations.

Figure 4:
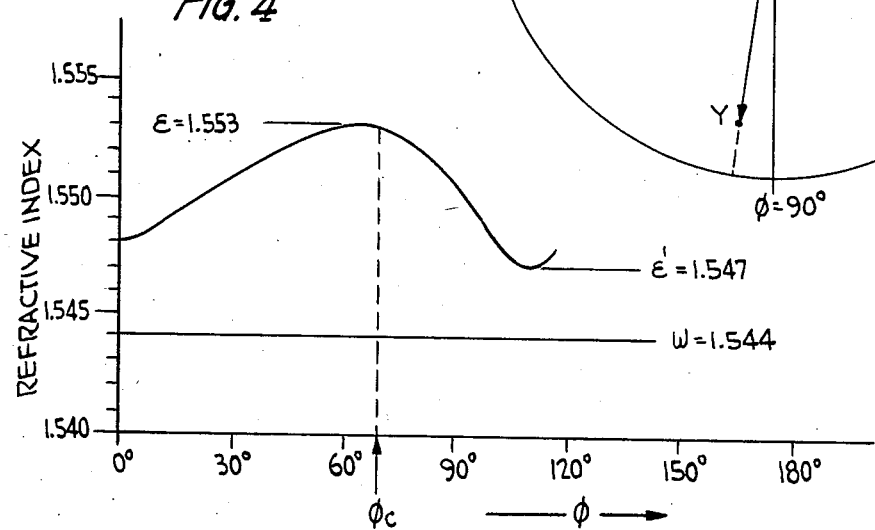
FIG. 4 is a plot of the refractive indices $\omega$, $\epsilon$ and $\epsilon'$ vs $\phi$; $\phi_c$ indicates the value of $\phi$ that orients this uniaxial crystal's c axis into the yz plane.

Uniaxial crystal specimens are much simpler to measure than biaxial crystal specimens. For uniaxial crystals, if the automated-refractometer-measured refractive indices are plotted versus phi angles, one of the two curves in FIG. 2 will become a straight line that corresponds to the refractive index $\omega$ in value (FIG. 4). The remaining curve will exhibit two extrema, one corresponding to $\epsilon$ in value, whereas the other will be an orientation-dependent refractive index "0" which will be somewhere between $\omega$ and $\epsilon$ in value as shown in FIG. 4. The $\phi$ value corresponding to the extremum most distant from the $\omega$ line, namely $\phi_c$, will indicate the angle between the plane containing the crystal's c-axis and the Cartesian yz plane. The angle of the c-axis (optic axis) relative to Cartesian axis z can be determined by use of the refractometer's rotatable polarizer or, using the values indicated in FIG. 4 for $\omega$, $\epsilon$ and "0", this angle can be calculated because:

$$\sin^2 \rho_c = \frac{\frac{1}{\epsilon'^2} - \frac{1}{\epsilon^2}}{\frac{1}{\omega^2} - \frac{1}{\epsilon^2}}$$

Thus, given $\epsilon = 1.553$, $\omega = 1.544$ and $0 = 1.547$, the angle $\rho_c$ is calculated to be 54.6 degrees.

The automated refractometer is programmed to translate a rock specimen or ceramic thin section specimen using x, y steps from 0.005 to 2.0 mm, more or less, depending upon how fine or course-grained the material is. At each x, y point where it is programmed to stop, it will measure, for the wavelengths used, the principal refractive indices. For biaxial crystals it will determine the orientation of X, Y, Z relative to Cartesian axes x, y, z, and for uniaxial crystal specimens it will determine the orientation of their single optic axis (c-axis) relative to x, y and z. For each point-of-call the computer will store: (1) the point's x, y coordinates; (2) the measured refractive indices n for isotropic materials; $\epsilon$, $\omega$ and "0" for uniaxial materials; $\alpha$, $\beta$, $\gamma$ and "0" for biaxial materials; and (3) the $\phi$ and $\rho$ coordinates of the single optic axis for uniaxial crystal specimens, or of the principal vibration axes X, Y and Z for biaxial crystal specimens.

After the automated refractometer completes its scan of a thin section specimen, its computer will analyze the data and print:

(1) The percentage of x, y points at which phase A was encountered, phase B, phase C, etc. These will provide estimates of the volume percentages of phases A, B, C, etc., in the specimen or synthetic material scanned. It will have differentiated the grains of phase A from those of phase B and C, etc., by their differing principal refractive indices. Ultimately, the memory bank of the computer will be fed with the known principal indices of many natural and synthetic compounds so that, for each phase A, B, C, etc., it will be able to furnish its identity, or supply a list of several possibilities for its true identity.

Figure 5:
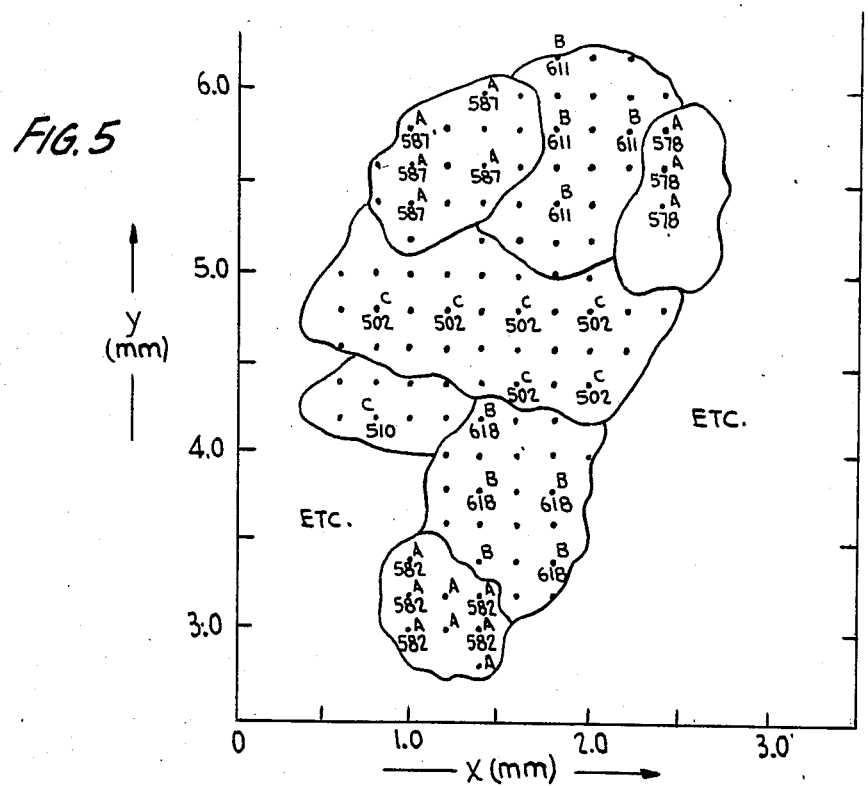
FIG. 5 is a map of a thin section of a specimen as plotted by the computer of the invention.

(2) A scaled-up map as shown in FIG. 5 of the thin section specimen showing the shapes of the grains of the various different components A, B, C, etc. For a thin section specimen consisting entirely of quartz grains, the automated refractometer would differentiate one differently oriented quartz grain from another because, although their principal refractive indices were the same, they would possess different values of the orientation-controlled index "0" and/or different $\phi$ angles for their c (optic) axis. Neighboring, but differently oriented, grains of the same biaxial substance would be similarly differentiated by differing values of the orientation-controlled refractive index 0 and by differing $\phi$ values for X, Y and Z.

(3) A Measure of the average garin size for each phase A, B, C . . . could be obtained by determining, for example for phase A, the average number of x, y points-of-call for grains of A. For example, assume that 4000 of the total points of the x, y grid occurred on 800 grain-cross-sections of phase A. This average of five points per grain would indicate an average cross-section of 5 times $x_t$ times $y_t$, where $x_t$ and $y_t$ represent the translation distances used along x and y during the scan by the refractometer. Alternatively, or in addition, the cross-sectional area of each grain of, for example, phase A could be calculated. Then a higtogram could be prepared to show the frequency distribution of these cross-sectional areas within user-selected size-classes. Additionally, the computer could determine directions of elongation for the grain cross-sections in the xy plane and then plot a rose "diagram" to show whether there was any preferred dimensional elongation within this xy plane.

(4) Petrofabric diagrams for each anisotropic phase, one for component A, one for B, etc. Currently, geologists rarely compile petrofabric diagrams for biaxial crystal specimens because the time required is so prohibitive. This capability of the automated refractometer should provide new impetus to structural geology both in academia and in industry.

The refractive indices of a liquid being produced or used in a commercial process and measured by the automated refractometer can be monitored continuously by equipping the refractometer with a liquid-flow-through sample holder in place of the x-, y-translatable and z rotatable one. Beyond-tolerance deviations of the liquid's refractive index from the refractive index for the ideal composition generate, in a feed-back control loop of the automated refractometer, an error signal that activates a warning bell or buzzer. The effect of ambient temperatures on the liquid's refractive index could be controlled (1) by running the liquid specimen through coils of metal tubing in a constant-temperature bath, or (2) by automatic electronic correction of the ambient refractive index to its value at the standard temperature.

FIG. 5 illustrates a portion of a map of a thin-section specimen as it would appear if printed from the measured refractive data by the computer. The dots represent x, y points where the automated refractometer stopped to measure refractive indices. By printing phase A, phase B and phase C near these points, the refractometer indicates that crystal specimens of three different materials were encountered. The printed numbers represent the orientation-controlled index "0", with 1.0 subtracted from it, and multiplied by 1000. Thus "502" actually represents the orientation-controlled index 1.502. The boundary between two differently oriented grains of C can be established because the orientation-controlled index is 1.502 for the one grain, but 1.510 for the other.

Figure 6:
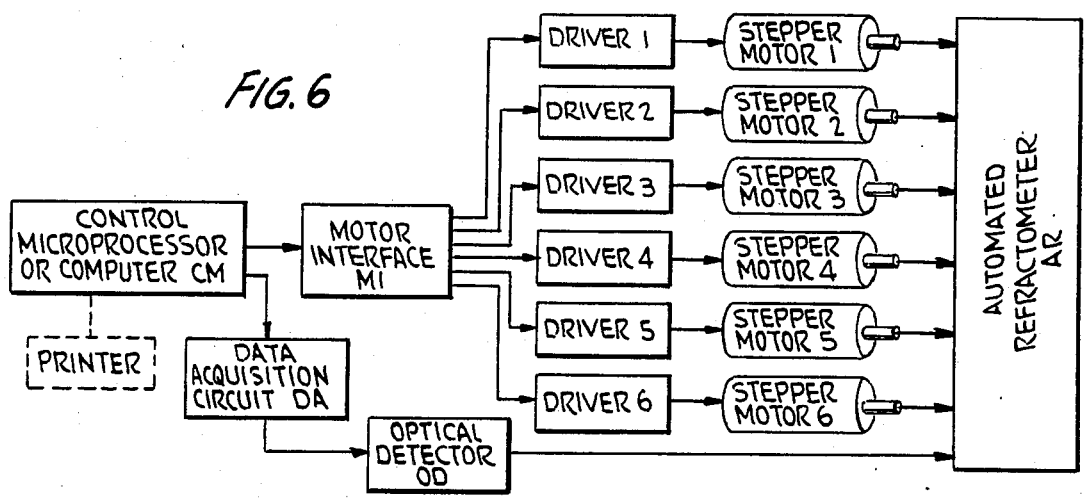
FIG. 6 is a block diagram showing typical control circuitry for the present invention and is subject to modification and improvement as more powerful computer chips become available.

The automated refractometer (AR) optically scans a specimen by means of a computer-controlled positioning and data acquisition system as shown schematically in FIG. 6. The AR's control microprocessor (CM) will operate the entire system by interfacing the operator with motor interface circuit MI, drivers No. 1, No. 2, No. 3, No. 4, No. 5 and No. 6, individual stepper motors 1, 2, 3, 4, 5 and 6, data acquisition circuit DA and optical detector OD. The computer CM controls the AR and makes the necessary calculations to extract the information from the raw measured data. The motor interface circuit MI enables the computer CM to communicate with the driver circuits No. 1–No. 6. These circuits interpret the control signals sent from computer CM and encode it in the necessary form to control the stepper motors 1–6. Driver circuits No. 1–No. 6 include the power source for stepper motors 1–6. The optical detctor OD measures the light intensity from the output of the AR. The data acquisition circuit DA converts the measured light intensity signals into a form recognizable but the digital computer CM. Stepper motors 1–6 respectively move the sample specimen from one grid point to another on the x-y plane, rotate the grid point about the z-axis, rotate the two planar mirrors RM1 and RM2, and insert and rotate the withdrawable polarizer.

The operator can specify either automatic or manual scanning using appropriate inputs to the control microprocessor CM. For automatic scanning, all stepper motors 1–6 are first used to return the mechanical system to a reference position. Assume that at this position the incident laser beam radiation source (not shown) interacts with a portion of one mineral grain of the specimen. The receiver angle is then varied and the optical detector OD output is monitored to determine if total internal reflection occurs. If it does, the incident angle is decreased and the receiver angle scanned again. If not, the critical angle information is stored in the memory of computer CM, and the x or y position of the sample is incremented. This procedure is repeated for every x, y location on the sample and a corresponding array of data is stored in the computer memory. A map of the sample (containing index values and optical indicatrix orientation) may then be printed by a printer associated with the computer CM.

For manual scanning, the operator may specify those precise x, y locations on the sample at which the automated refractometer is commanded to measure the principle refractive indices and orientations for the crystals or other solids occurring there. Alternatively, the operator may specify the initial point and the bounding points of a limited area that is to be scanned and measured automatically by the automated refractometer.

The automated refractometer method and apparatus provides both mechanical and computational flexibility in addition to simple positioning and data recording. This is accomplished by means of simple user commands; the position, step sizes, scan rates, and dwell times of each position are easily varied. Also a variety of mathematical calculations on the recorded data may be performed without uploading to a full scale mainframe computer.

The method and apparatus of the automated refractometer obtains the following goals:

(1) Rotation of angle $\phi$ by increments commensurate with the accuracy desired.

(2) Sample specimen x, y translation by small, selected increments, eg. 0.1 or 0.05 mm.

(3) Input rotatable mirror (RM1) adjustable to the nearest 0.01 degrees.

(4) Output rotatable mirror (RM2) adjustable to the nearest 0.01 degrees.

(5) Enables automatic scan and point-by-point manual measurements.

(6) Enables measurements at three or more visible or non-visible wavelengths.

(7) Allows for microscope viewing of the sample specimen.

(8) Allows for beam focus spot diameter equal to or less than 0.1 mm.

(9) Measures the critical angle(s) exhibited by a solid or liquid for each value of $\phi$.

(10) Allows for print out of calculated data in plot format.

When light or other radiation passes from the refractometer's hemicylinder into the sample, the value of the critical angle (CA) will depend upon (1) the refractive index of the hemicylinder, and (2) that of the sample. Thus, as Table 1 illustrates, a critical angle of 45 degrees would indicate a sample index of 1.5203 for a hemicylinder of index 2.15, of 1.3435 (for a 1.90 hemicylinder), of 1.2021 (for a 1.70 hemicylinder), or of 1.0607 (for 1.50 hemicylinder). Comparison of the columns headed 2.15, 1.90, 1.70 and 1.50 discloses that dn/dCA, the rate of change of sample index n versus the rate of change of critical angle CA, is smallest, and thus the sensitivity of the method and apparatus of the refractometer is greatest, if the index of the hemicylinder in use does not by too much exceed that of the sample being measured. Consequently, a sample whose refractive index approximately equals 1.49 would be more precisely measured using a 1.50 hemicylinder than a 2.15 hemicylinder. Table 1 substantiates this statement by showing that, if a refractive index of about 1.49 is being measured, dn/dCA approximately equals 0.027 per one degree if the 2.15 hemicylinder is being used, but only about 0.003 per one degree if the 1.50 hemicylinder is being used.

Figure 7:
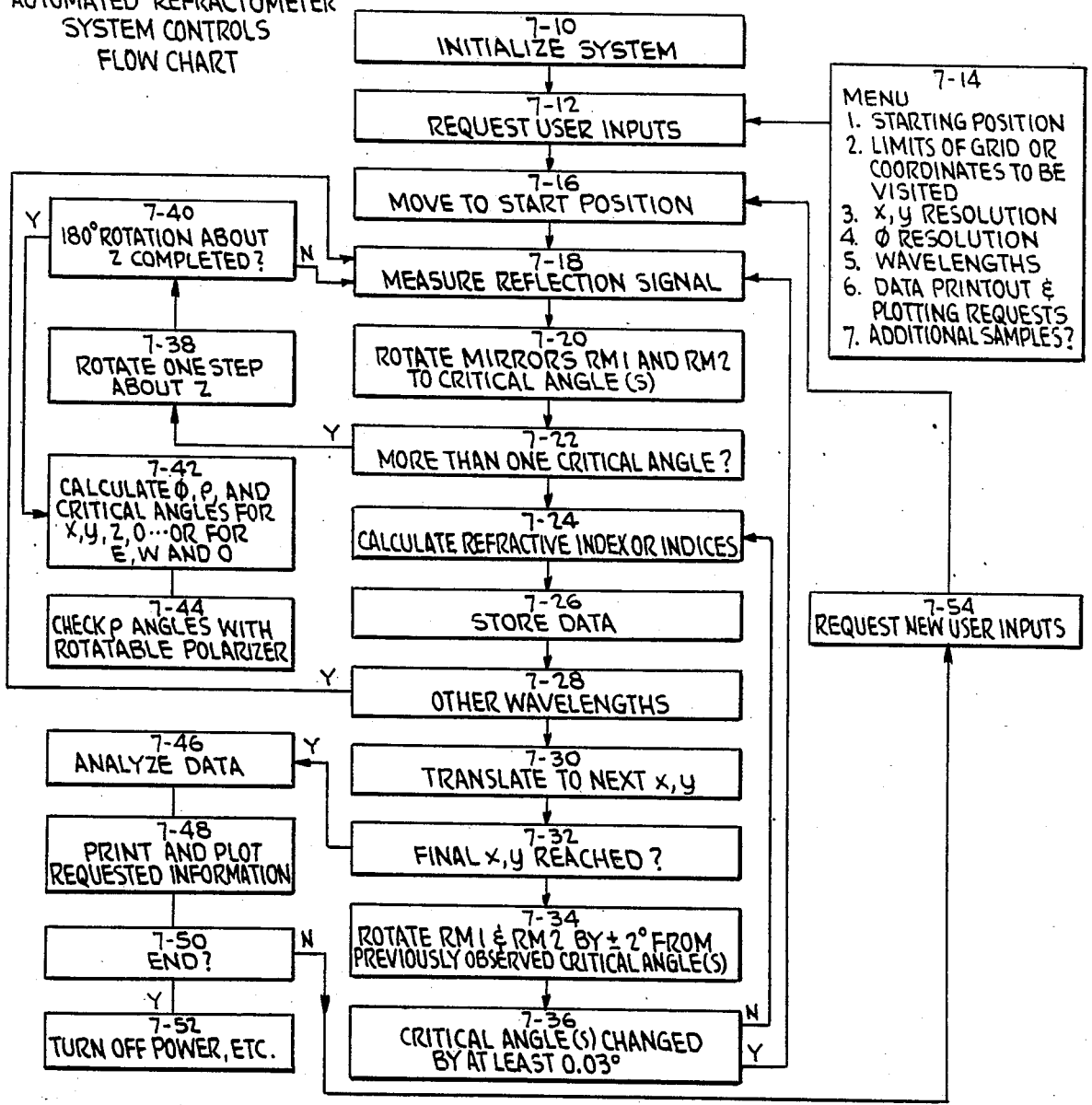
FIG. 7 shows an exemplary systems control flow chart for the automated refractometer.

FIG. 7 represents a system controls flow chart for the automated refractometer. The automated system is entered in step 7–10 by inserting the parameters that initialize the system. The system then proceeds to step No. 7–12 where the computer requests user inputs from a menu as shown in step No. 7–14 as follows:

1. Starting Position
2. Limits of Grid or Coordinates to be Visited
3. x, y Resolution
4. Theta Resolution
5. Wavelengths
6. Data Printout and Plotting Requests
7. Additional samples?

The program then flows to step No. 7–16 "Move to Start Position" wherein the AR's computer causes the stepper motor (shown in FIG. 6) to move the sample specimen to the zero grid position, and then flows to step No. 7–18 to measure a reflection signal as described, supra. Planar mirrors RM1 and RM2 are then rotated (step No. 7–20) to determine (1) the single critical angle of isotropic materials or (2) the two critical angles for anisotropic materials. At step No. 7–22 the program branches and, for anisotropic crystals, enters a loop (Steps No. 7–38 to 7–40 to 7–18 to 7–20 to 7–22) whereby the materials's two critical angles are measured as $\phi$ is incremented. After a 180° rotation around z is completed, the system leaves the loop and flows into step No. 7–42. At this point its gathered data define two curves resembling FIG. 2, except that critical angles (CA) and not refractive indices are plotted versus $\phi$. Points on these curves where the first derivative d CA/d $\phi$ equals zero represent for biaxial crystals $\phi_X$, $\phi_Y$, $\phi_Z$, and $\phi_O$ or for uniaxial crystals, $\phi_c$ and $\phi_O$. A rotatable polarizer, if inserted to intercept the electromagnetic beam prior to its entry into the detector (step No. 7–44), will determine the angles $\rho_X$, $\rho_Y$ and $\rho_Z$ for biaxial crystals and differentiate the β vibration direction from the "0" vibration direction. The angles $p_X$, $p_Y$ and $p_Z$ can also be calculated using the equations on pp. 18–19. The system next flows into step No. 7–24 in which the critical angle(s) observed for the principal index n of an isotropic material or for principal indices ε, ω or α, β and γ of anisotropic materials are converted to the actual values of these refractive indices for the electromagnetic wavelength in use. The system then stores the data (step No. 7–26) and enters step No. 7–28. If measurements are to be performed at another wavelength, the system loops back to step No. 7–18. After this loop is completed for each menu-specified wavelength, the system flows to step No. 7–30 and translates the thin section to the next x, y point. Step No. 7–32 checks whether all menu-stipulated x, y points have been visited. If 'yes,' the system flows into steps No. 7–46 and 7–48, in which it analyzes the data, prints and plots requested information, histograms, petrofabric diagrams, etc. It next queries as to whether the measurements are at end (step No. 7–50). If 'yes,' it enters step No. 7–52 and shuts down the automated refractometer. If 'no,' the system enters step No. 7–54 to request new instructions and, this done, re-enters the system at step No. 7–16 to begin another study.

Figure 8A:
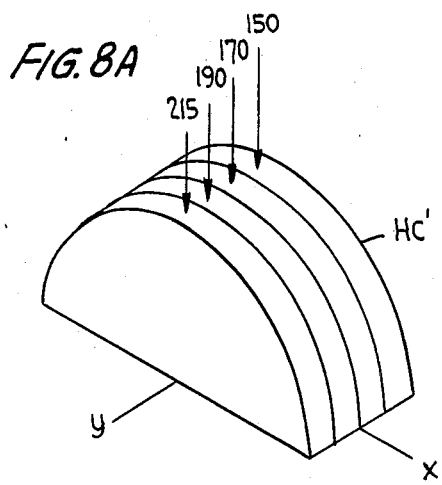
FIGS. 8A and 8B are modified embodiments of hemicylinders for use with the method and apparatus of the present invention.

An advantage of the method and apparatus of the automated refractometer over existing refractometers is that its design will permit it to operate with maximum precision and sensitivity over a wide range of refractive indices. This can be achieved by use of the laminated hemicylinder consisting of approximately 3 mm thick wafers with differing refractive indices (FIG. 8A). Thus, simply by translating the hemicylinder along y, the lamina of optimum refractive index relative to the sample being measured would become the operative part of the hemicylinder. Only four wafers are shown laminated in FIG. 8A, but more could be used if desired.

Figure 8B:
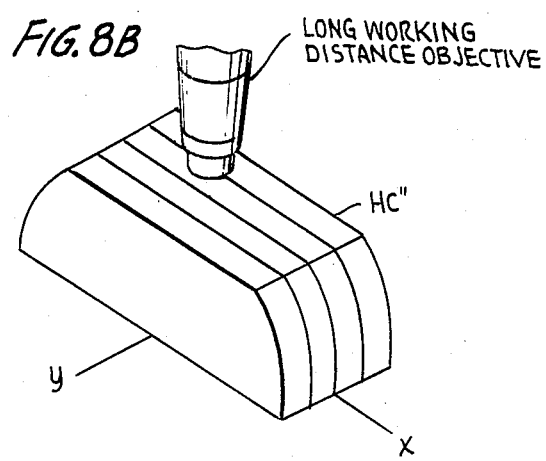

Refractive indices ordinarily exceed 1.0. Thus, as Table 1 illustrates, critical angles less that 28 degrees will not occur with a hemicylinder of index 2.15 or less. Accordingly, it is possible to polish a flat surface on the top of the hemicylinder as shown in FIG. 8B and to equip the automated refractometer with a telescope or long-working-distance objective, so that a crystal specimen being measured by the automated refractometer method and apparatus can be visually inspected if desired.

It is recognized by those skilled in the art of measuring refractive indices that a hemisphere could be substituted for the hemicylinder described herein. Similarly, a prism could also be used in place of the hemisphere or the hemicylinder.

The method and apparatus of the invention is also intended to cover the miniaturization of a Pulfrich or Abbe refractometer so that it could be used with (a) an intense finely collimated incident beam, (b) an x, y translatable and z rotatable sample holder, and (c) a photometric means of measuring critical angles.

It is also the intention of the present invention to include the concept of combining extremely fine collimation of the refractometer's incident beam with (1) computer-controlled x, y translation and z rotation of the sample holder; (2) photometric determination of critical angles; and (3) computer analysis of the data so that the computer can (a) identify each solid component and plot its grain shapes on an enlarged map of the thin section, (b) plot a petrofabric diagram of each anisotropic component, (c) calculate the average grain size for each component and (d) determine each component's percent by volume in the thin section so that, after this is done, for example for all the minerals in a rock, the specimen may be identified and classified by comparison with authoritative volumetric classifications for known rocks as stored in the memory of the computer.

It is also believed by the inventor that the use of the orientation-controlled index "0" is novel and non-obvious method of establishing grain boundaries between identical but differently oriented crystals in a thin section.

Figure 9:
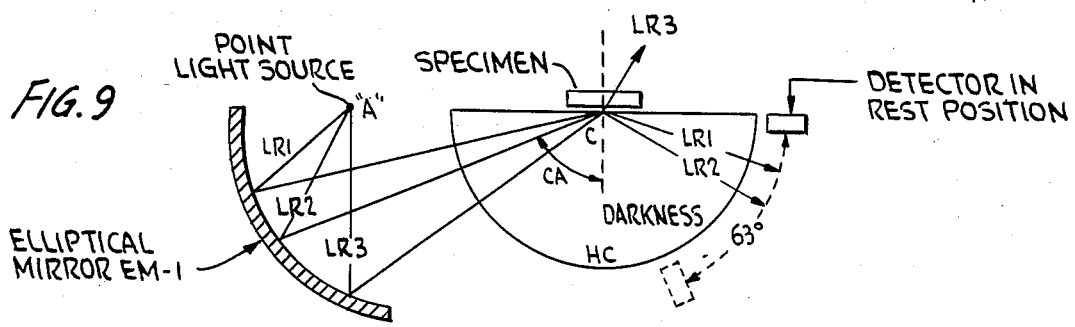
FIG. 9 illustrates a point source of light and movable detector in accordance with the present invention.

A less effective modification of the automated refractometer would involve the elimination of one or both of the elliptical mirrors. For example, both such mirrors might be replaced by a finely collimated incident beam and a finely collimated photometric receptor for the reflected beam where such beams scan through the equal but opposite angles $\theta_I$ and $\theta_R$. Also, another modification would involve the use of one elliptical mirror to illuminate the hemicylinder with either a rotating mirror at A (FIG. 1) or with a point source of light at A as illustrated in FIG. 9. The critical angle could then be measured by slowly changing the position of a single detector from a rest position in FIG. 9 through an angle of 63 degrees, greater excursion not being needed because the critical angles less than 27 degrees could only occur if the refractive index of the unknown specimen were less than 1.0 (reference Table 1).

Alternatively, the hemicylinder could be illuminated by other means and the single detector shown in FIG. 9 could be used to determine the critical angle.

Figure 10A:
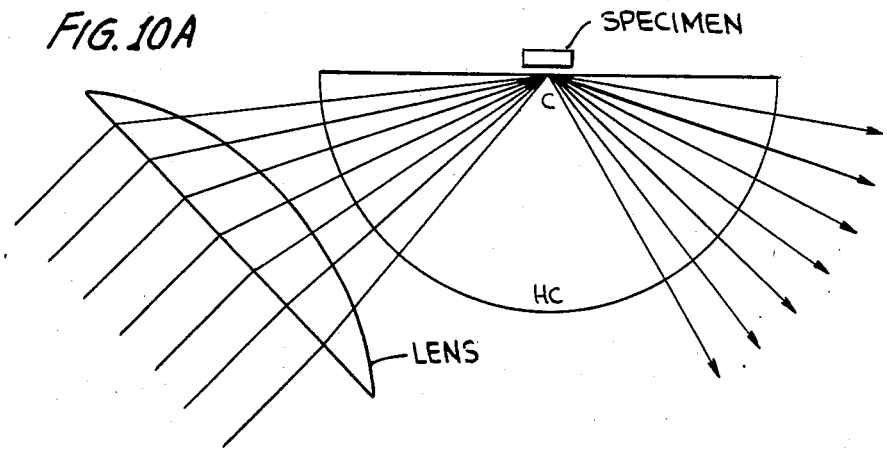
FIGS. 10A and 10B illustrate the use of alternative illumination of the hemicylinder in accordance with the present invention.
Figure 10B:
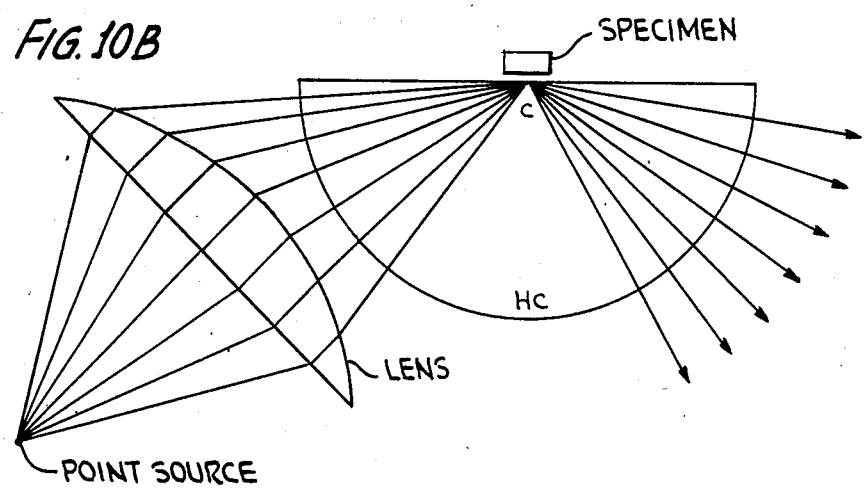
Figure 11A:
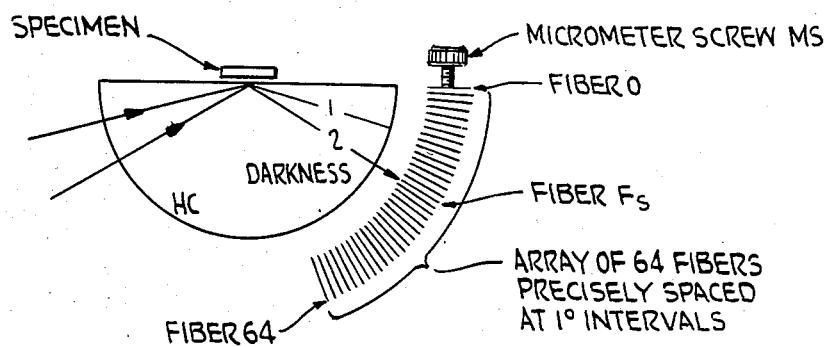
FIGS. 11A and 11B show arrays of optical fibers to determine critical angles in accordance with a modified embodiment of the present invention.
Figure 11B:
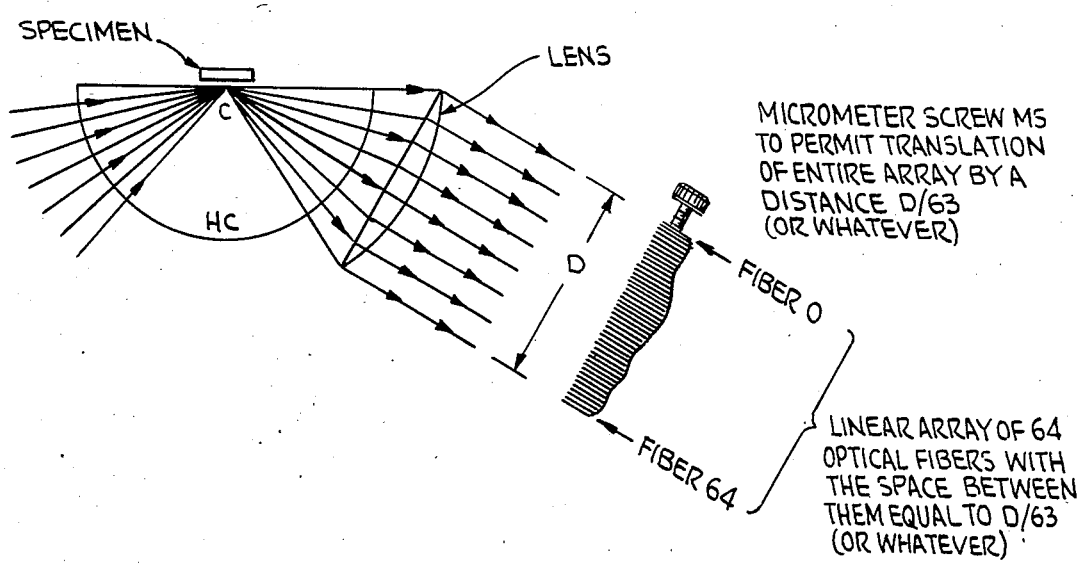

Different methods of illuminating the hemicylinder include the use of a lens, achromatic or otherwise, to collect parallel rays as shown in FIG. 10A or diverging rays from a point source as shown in FIG. 10B and focus them to a point that would coincide with C, the origin of the Cartesian coordinate system as defined herein. The critical angle could then be determined from 64 optical fibers arranged at one degree intervals in a radial array as shown in FIG. 11A and each having its own detector. By use of a micrometer screw, the entire radial array could be rotated up to one degree around C so as to measure the critical angle to a fraction of a degree. Alternatively, the totally reflected rays could be collected by a lens whose principal focus coincided with C as shown in FIG. 11B. In such a case, after passing through the lens, all of the totally reflected rays would travel parallel to the lens's axis. If D represents the diameter of this lens, then the 64 optical fibers could be arranged at intervals corresponding to D/63. A micrometer screw could be used to translate linearly the entire array so as to measure the critical angle to within a fraction of a degree. Each fiber could lead to its own detector; alternatively, a television image of the end views of the 64 fibers could be scanned before and after translation of the array from its rest position by the micrometer screw.

Chromatic aberration may occur in any optical system that employs lenses and/or prisms, but not for one that employs mirrors. In achromatic or "color-corrected" lenses, chromatic aberration is customarily eliminated for two colors, usually red and blue, and greatly reduced for the remaining visible wavelengths as well as for infrared wavelengths up to 800 or 900 nm. However, for wavelengths approaching or exceeding 1200 nm, the correction becomes increasingly less effective. On the one hand, the refractometer design shown in FIG. 1 eliminates the possibility of chromatic aberration. Its mirrors are not subject to it, and they always reflect the "light" rays so that they are normally incident upon the hemicylinder's curved surface. This design of refractometer is thus operative over a wide range of wavelengths (ultraviolet, visible, infrared), whereas refractometers employing lenses and/or prisms will be hampered by chromatic aberration if operated at infrared wavelengths. The only restraint on the range of wavelengths this present refractometer can use will be the hemicylinder's ability to transmit these wavelengths. Since the hemicylinder can be made of diamond or cubic zirconia, it should be able to function over an exceedingly wide range of wavelengths, including those well outside the visible range.

In FIG. 9, the use of a point source of light located at one of the two foci of an elliptical mirror with the hemicylinder or hemisphere centered at the mirror's focus is illustrated. Considering only light rays LR1, LR2 and LR3, after reflection by the elliptical mirror EM1', light ray LR1 impinges at greater than the critical angle, light ray LR2 impinges at precisely the critical angle, and light ray LR3 impinges at less than the critical angle. Light ray LR3 therefore enters the crystal specimen, passes through it, and is absorbed by a black background in the sample holder (not shown). A single detector PD, movable from a rest position through an angle of 63 degrees, would pinpoint the boundary between darkness and light to measure the critical angle CA, or its complement.

With respect to FIGS. 11A and 11B, as shown in FIG. 11A, a radial array of 64 optical fibers is spaced precisely at one degree intervals relative to hemicylinder HC centered at C. The micrometer screw MS, if actuated manually or by a stepper motor, would rotate the entire array of fibers OF around point C by up to one degree. Thus if fiber $F_s$ were the fiber most distant from from fiber 0 that still transmitted light, and if its angle relative to 0 were 18 degrees, then if a 0.55 degree micrometer-screw-actuated rotation of the fiber array caused fiber $F_s$ to transmit light no longer, the critical angle would be 90 degrees−18.55 degrees or 71.45 degrees.

In FIG. 11B, a lens, achromatic or otherwise, is installed so that its principal focus falls at C. D represents the minimum diameter of the lens. Consequently, all light rays emanating from point C will be made parallel after passage through the lens. An array of 64 parallel optic fibers, plus provisions to translate the entire array by D/63 will permit precise measurement of the critical angle.

It is to be understood that the automated refractometer described herein is capable of operating with light wavelengths within the ultraviolet, visible, and/or infrared. The light radiating source (not shown in the various Figures) can be a monochromatic source, such as a laser bem, or a continuous source of radiation with appropriate filters being used to obtain the desired wavelength for irradiation of the specimen within the automated refractometer (as illustrated in FIG. 1). Provision is made within the computer CM (FIG. 6) to accommodate the aforementioned wavelength spectrum by inclusion in the menu 7-14 ("5. Wavelength(s)") as shown in the system controls flow chart of FIG. 7. The operator of of the automated refractometer system inserts the wavelength data along with the other information in the "Request User Inputs" step No. 7-12 of the system flow control.

Step No. 7-48 ("Print and Plot Requested Information") in the system controls flow of FIG. 7 is accomplished by a printer PR illustrated in FIG. 6 in phantom lines as being controlled by the automated refractometer's computer CM. It is also to be understood that a readout of the automated refractometer can be visually displayed by a conventional crt display terminal associated with the automated computer CM as is known to those skilled in the computer arts. Moreover such display terminals are commonly used with computers in accordance with the present day computer technology.

The components used with the automated refractometer are known to those skilled in the art of refractometry and computer technology, unless specified otherwise herein. The system controls flow chart illustrated in FIG. 7 is capable of being programmed in any program language presently known to computer technology.

The above-described embodiments of the invention are intended to be only illustrative of the invention to enable the invention to be practiced. Various modifications and alterations will be apparent to those skilled in the refractive measurement art. The invention is not intended to be limited by, or to, the specific embodiments described herein, but to be accorded the full range of equivalents of the elements and components set forth in the appended claims.

TABLE 1

| | REFRACTIVE INDEX OF HEMICYLINDER | | | |
|---|---|---|---|---|
| CA | 2.15 | 1.90 | 1.70 | 1.50 |
| 27 | 0.9761 | 0.8626 | 0.7718 | 0.6810 |
| 28 | 1.0094 | 0.8892 | 0.7981 | 0.7042 |
| 29 | 1.0423 | 0.9211 | 0.8242 | 0.7272 |
| 30 | 1.0750 | 0.9500 | 0.8500 | 0.7500 |
| 32 | 1.1393 | 1.0068 | 0.9009 | 0.7949 |
| 33 | 1.1710 | 1.0348 | 0.9259 | 0.8170 |
| 34 | 1.2023 | 1.0625 | 0.9506 | 0.8386 |
| 35 | 1.2332 | 1.0898 | 0.9751 | 0.8604 |
| 36 | 1.2637 | 1.1168 | 0.9992 | 0.8817 |
| 37 | 1.2939 | 1.1434 | 1.0231 | 0.9027 |
| 38 | 1.3237 | 1.1698 | 1.0466 | 0.9235 |
| 39 | 1.3530 | 1.1957 | 1.0698 | 0.9440 |
| 40 | 1.3820 | 1.2213 | 1.0927 | 0.9642 |
| 41 | 1.4105 | 1.2465 | 1.1153 | 0.9841 |
| 42 | 1.4386 | 1.2713 | 1.1375 | 1.0037 |
| 43 | 1.4663 | 1.2958 | 1.1594 | 1.0230 |
| 44 | 1.4935 | 1.3199 | 1.1809 | 1.0420 |
| 45 | 1.5203 | 1.3435 | 1.2021 | 1.0607 |
| 46 | 1.5466 | 1.3667 | 1.2229 | 1.0790 |
| 47 | 1.5724 | 1.3896 | 1.2433 | 1.0970 |
| 48 | 1.5978 | 1.4120 | 1.2633 | 1.1147 |
| 49 | 1.6226 | 1.4339 | 1.2830 | 1.1321 |
| 50 | 1.6470 | 1.4555 | 1.3023 | 1.1491 |
| 51 | 1.6709 | 1.4766 | 1.3211 | 1.1657 |
| 52 | 1.6942 | 1.4972 | 1.3396 | 1.1820 |
| 53 | 1.7171 | 1.5174 | 1.3577 | 1.1980 |
| 54 | 1.7394 | 1.5371 | 1.3753 | 1.2135 |
| 55 | 1.7612 | 1.5564 | 1.3926 | 1.2287 |
| 56 | 1.7824 | 1.5752 | 1.4094 | 1.2436 |
| 57 | 1.8031 | 1.5935 | 1.4257 | 1.2580 |
| 58 | 1.8233 | 1.6113 | 1.4417 | 1.2721 |
| 59 | 1.8429 | 1.6286 | 1.4572 | 1.2858 |
| 60 | 1.8620 | 1.6454 | 1.4722 | 1.2990 |
| 61 | 1.8804 | 1.6618 | 1.4869 | 1.3119 |
| 62 | 1.8983 | 1.6776 | 1.5010 | 1.3244 |
| 63 | 1.9157 | 1.6929 | 1.5147 | 1.3365 |
| 64 | 1.9324 | 1.7077 | 1.5279 | 1.3482 |
| 65 | 1.9486 | 1.7220 | 1.5407 | 1.3595 |
| 66 | 1.9641 | 1.7357 | 1.5530 | 1.3703 |
| 67 | 1.9791 | 1.7490 | 1.5649 | 1.3808 |
| 68 | 1.9934 | 1.7616 | 1.5762 | 1.3908 |
| 69 | 2.0072 | 1.7738 | 1.5871 | 1.4004 |
| 70 | 2.0203 | 1.7854 | 1.5975 | 1.4095 |
| 71 | 2.0329 | 1.7965 | 1.6074 | 1.4183 |
| 72 | 2.0448 | 1.8070 | 1.6168 | 1.4266 |
| 73 | 2.0561 | 1.8170 | 1.6257 | 1.4345 |

TABLE 1-continued

| | REFRACTIVE INDEX OF HEMICYLINDER | | | |
|---|---|---|---|---|
| CA | 2.15 | 1.90 | 1.70 | 1.50 |
| 74 | 2.0667 | 1.8264 | 1.6341 | 1.4419 |
| 75 | 2.0767 | 1.8353 | 1.6421 | 1.4489 |
| 76 | 2.0861 | 1.8436 | 1.6495 | 1.4554 |
| 77 | 2.0949 | 1.8513 | 1.6564 | 1.4616 |
| 78 | 2.1030 | 1.8585 | 1.6629 | 1.4672 |
| 79 | 2.1105 | 1.8651 | 1.6688 | 1.4724 |
| 80 | 2.1173 | 1.8711 | 1.6742 | 1.4772 |
| 81 | 2.1235 | 1.8766 | 1.6791 | 1.4815 |
| 82 | 2.1291 | 1.8815 | 1.6835 | 1.4854 |
| 83 | 2.1340 | 1.8858 | 1.6873 | 1.4888 |
| 84 | 2.1382 | 1.8896 | 1.6907 | 1.4918 |
| 85 | 2.1418 | 1.8928 | 1.6935 | 1.4943 |
| 86 | 2.1448 | 1.8954 | 1.6959 | 1.4963 |
| 87 | 2.1471 | 1.8974 | 1.6977 | 1.4979 |
| 88 | 2.1487 | 1.8988 | 1.6990 | 1.4991 |
| 89 | 2.1497 | 1.8997 | 1.6997 | 1.4998 |

What is claimed is:

1. An optical refractometer capable of being adapted for automatically determining the principal indices of a specimen, comprising:
   a means for receiving an incident radiation beam;
   a first elliptical mirror having first and second foci;
   a first rotatable surface for reflecting said incident radiation beam onto a reflecting surface of said first elliptical mirror and having an axis of rotation extending through said first focus of said first elliptical mirror;
   a hemicylinder having a center of curvature at said second focus of said first elliptical mirror and including means for rotatably mounting and translating a specimen respectively about a first axis and along a second and third axes such that a portion of said specimen is located at said second focus to receive the reflected incident beam from said first rotatable surface;
   a second elliptical mirror having third and fourth foci; and a second rotatable surface for reflecting the incident radiation beam from said second elliptical mirror and having an axis of rotation extending through said fourth focus, said third focus being at said first axis coincident with said second focus for producing a reflected beam output.

2. An optical refractometer as claimed in claim 1, further comprising means for controlling the rotation of said first and second rotatable surfaces for altering the angle of said incident radiation and the angle of said reflected beam output, and for rotating said specimen about said first axis and translating said specimen along said second and third axes, respectively.

3. An optical refractometer as claimed in claim 2, wherein said means for controlling the rotation simultaneously rotates said first and second rotatable surfaces through equal angle displacements.

4. An optical refractometer as claimed in claim 2, wherein said means for controlling the rotation rotates said first rotatable surface continuously, and said second rotatable surface is rotated in stepped increments.

5. An optical refractometer as claimed in claims 2, 3 or 4, wherein said means for controlling the rotation includes first, second, third, fourth and fifth stepper motors for respectively rotating said first and second rotatable surfaces, the rotation of said specimen about said first axis and the translation of said specimen along said second and third axes.

6. An optical refractometer as claimed in claims 2, 3 or 4, further comprising a polarizing element mounted for rotation about an axis including said reflected beam output and controlled by said means for controlling rotation.

7. An optical refractometer as claimed in claim 5, further comprising a control microprocessor for providing command signals to said means for controlling rotation and translation to successively alter the position of said first and second rotatable surfaces and the rotation and translation of said specimen in fixed increments to provide successive reflected beam outputs containing optical data relating to at least one principal refractive index of said specimen.

8. An optical refractometer as claimed in claim 7, further comprising an optical detector responsive to said reflected output beam, means for converting the output of said optical detector into digital signals for input to said control microprocessor.

9. An optical refractometer as claimed in claim 8, further comprising a printer controlled by said control microprocessor for providing a record of the optical data received by said control microprocessor.

10. An optical refractometer as claimed in claim 9, wherein said means for printing is controlled by said control microprocessor to produce a map of said specimen including points where the refractive indices of said specimen were measured and boundaries between different grains within said specimen.

11. An optical refractometer as claimed in claims 1, 2, 3 or 4, wherein said hemicylinder is a laminated element of materials having respectively different refractive indices, and said means for controlling rotation includes means for positioning a respective one of said materials to receive the reflected beam from said first elliptical mirror.

12. An optical refractometer as claimed in claim 5, wherein said hemicylinder is a laminated element of materials having respectively different refractive indices and said means for controlling rotation includes means for positioning a respective one of said materials to recieve the reflected beam from said first ellipitcal mirror.

13. An optical refractometer as claimed in claim 11, wherein a non-operative upper portion of said hemicylinder is cut off and polished parallel to said second and third axes along which said specimen is translated.

14. An optical refractometer as claimed in claim 13, further comprising a long working-distance objective positioned with respect to said polished portion of said hemicylinder to view the specimen being measured.

15. An optical refractometer as claimed in claims 1, 2, 3 or 4, wherein a point source of light is located at said first focus, and further comprising an optical detector movable from a rest position through a specified angle about said second focus for measuring the critical angle CA reflected from said specimen.

16. An optical refractometer as claimed in claim 5, wherein a point source of light is located at said first focus, and further comprising an optical detector movable from a rest position through a specified angle about said second focus for measuring the critical angle CA reflected from said specimen.

17. An optical refractometer as claimed in claims 1, 2, 3 or 4, wherein said means for receiving an incident radiation beam is a converging lens for focusing incident radiation towards said second focus.

18. An optical refractometer as claimed in claim 5, wherein said means for receiving an incident radiation beam is a converging lens for focusing incident radiation towards said second focus.

19. An optical refractometer as claimed in claims 1, 2, 3 or 4, wherein said first and second elliptical mirrors eliminate the possibility of chromatic aberration.

20. An optical refractometer as claimed in claim 5, wherein said first and second elliptical mirrors eliminate the possibility of chromatic aberration.

21. An optical refractometer as claimed in claims 1, 2, 3 or 4, further comprising means for optimizing a particular refractive index range.

22. An optical refractometer as claimed in claim 5, further comprising means for optimizing a particular refractive index range.

23. An optical refractometer as claimed in claim 11, further comprising means for optimizing a particular refractive index range.

24. An optical refractometer as claimed in claims 1, 2, 3 or 4, further comprising a flow-through sample holder and electrical feedback circuits responsive to said reflected beam output, and an annunciator responsive to said feedback circuits to provide a warning if the refractive index of the flow-through liquid being monitored varies beyond acceptable tolerances.

25. An optical refractometer as claimed in claim 5, further comprising a flow-through sample holder and electrical feedback circuits responsive to said reflected beam output, and an annunciator responsive to said feedback circuits to provide a warning if the refractive index of the flow-through liquid being monitored varies beyond acceptable tolerances.

26. An optical refractometer as claimed in claim 11, further comprising a flow-through sample holder and electrical feedback circuits responsive to said reflected beam output, and an annunciator responsive to said feedback circuits to provide a warning if the refractive index of the flow-through liquid being monitored varies beyond acceptable tolerances.

27. An optical refractometer as claimed in claim 17, further comprising a flow-through sample holder and electrical feedback responsive to said reflected beam output, and an annunciator responsive to said feedback circuits to provide a warning if the refractive index of the flow-through liquid being monitored varies beyond acceptable tolerances.

28. An optical refractometer as claimed in claim 1 wherein said receiving means, said first and second elliptical mirrors, said first and second rotatable surfaces and said hemicylinder are adapted to operate with light having wavelengths extending from and including the infrared to the ultraviolet.

29. An optical refractometer as claimed in claim 1, further comprising a withdrawable polarizing element positioned to intercept said reflected beam output, and microprocessor means for computing, whereby the precise orientation of vibration directions X, Y, Z and "0" for biaxial crystals can be determined by said microprocessor means from the value for the crystal's extrema $\phi_X$, $\phi_Y$, $\phi_Z$ and $\phi_O$ and from their angles relative to a Cartesian axis z, namely angles $\rho_X$, $\rho_Y$, $\rho_Z$ and $\rho_O$, these latter angles being determinable by rotating said polarizer so as to change the angle between its plane of polarization and axis z.

30. An optical refractometer as claimed in claim 2, further comprising a withdrawable polarizing element positioned to intercept said reflected beam output and means for computing, and wherein, if $\phi_X$, $\phi_Y$, $\phi_Z$ are known, then $\rho_X$, $\rho_Y$ and $\rho_Z$ are calculated by said microprocessor means using formulas:

$$\tan^2 \rho_X = - \frac{\cos(\phi_Z - \phi_Y)}{\{\cos(\phi_Y - \phi_X)\}\{\cos(\phi_Z - \phi_Y)\}}$$

$$\tan^2 \rho_Y = - \frac{\cos(\phi_Z - \phi_X)}{\{\cos(\phi_Y - \phi_Z)\}\{\cos(\phi_X - \phi_Y)\}}$$

$$\tan^2 \rho_Z = - \frac{\cos(\phi_Y - \phi_X)}{\{\cos(\phi_Z - \phi_X)\}\{\cos(\phi_Y - \phi_Z)\}}$$

31. An optical refractometer as claimed in claim 2, further comprising a withdrawable polarizing element positioned to intercept said reflected beam output and microprocessor means for computing, and wherein for uniaxial crystals the orientation of their single optic axis is determined from extremum value $\phi_C$ and from $\rho_C$, its angle relative to a Cartesian axis z, as calculated from equation:

$$\sin^2 \rho_c = \frac{\frac{1}{\epsilon'^2} - \frac{1}{\epsilon^2}}{\frac{1}{\omega^2} - \frac{1}{\epsilon^2}}$$

and wherein said withdrawable polarizing element is used to check the calculated values.

32. An optical refractometer as claimed in claim 29, wherein said command signals cause said means for controlling rotation and translation to successively alter the position of said first and second rotatable surfaces, and the rotation and translation of said specimen in fixed increments to provide successive reflected beam outputs containing optical data representing a scan of a thin section of a polycrystalline solid, and subsequent to said microprocessor means determining the optic orientation of each individual anisotropic crystal, said microprocessor means compiling data for a petrofabric diagram summarizing the extent and nature of each different anisotropic phase present in the solid, and further comprising means for plotting said petrofabric diagram.

33. An optical refractometer as claimed in any one of claims 1, 28 or 29 wherein the major axis of said first and second elliptical mirrors is at an angle less than 180 degrees.

34. An optical refractometer as claimed in any one of claims 1, 28 or 29, wherein said first and second elliptical mirrors differ from one another with respect to values of their respective major and minor axes, and with respect to value of their eccentricity.

35. An optical refractometer as claimed in any one of claims 1, 28 or 29, wherein said means for receiving a radiation beam receives finely collimated radiation beams whereby refractive indices are measured for exceedingly small areas of the specimen, and measurements of the principal refractive indices at various wavelengths can be made for very small grains or for relatively fine points on cross-sections of rocks, ceramics, or optical fibers.

36. An optical refractometer as claimed in claim 16, further comprising means for optimizing a particular refractive index range.

37. An optical refractometer as claimed in claim 16, further comprising a flow-through sample holder and electrical feedback circuits responsive to said reflected beam output, and an annunciator responsive to said feedback circuits to provide a warning if a refractive index of the flow-through liquid being monitored varies beyond acceptable tolerances.

38. An optical refractometer as claimed in claim 29, wherein said command signals cause said means for controlling rotation and translation to successively alter the position of said first and second rotatable surfaces, and the rotation and translation of said specimen in fixed increments to provide successive reflected beam outputs containing optical data representing a scan of a thin section of a polycrystalline solid, and subsequent to said microprocessor means determining the optic orientation of each individual anisotropic crystal, said microprocessor means compiling data for a petrofabric diagram summarizing an extent and nature of each different anisotropic phase present in the solid, and further comprising means for plotting said petrofabric diagram.

39. An optical refractometer as claimed in claim 7, wherein the major axis of said first and second elliptical mirrors is at an angle less than 180 degrees.

40. An optical refractometer as claimed in claim 7, wherein said first and second elliptical mirrors differ from one another with respect to values of their respective major and minor axes, and with respect to value of their eccentricity.

41. An optical refractometer as claimed in claim 7, wherein said means for receiving a radiation beam receives finely collimated radiation beams whereby refractive indices are measured for exceedingly small areas of the specimen, and measurements of the principal refractive indices at various wavelengths can be made for very small grains or for relatively fine ponts on cross-sections of rocks, ceramics, or optical fibers.

42. An optical refractometer as claimed in claim 32, wherein said means for receiving a radiation beam receives finely collimated radiation beams whereby refractive indices are measured for exceedingly small areas of the specimen, and measurements of the principal refractive indices at various wavelengths can be made for very small grains or for relatively fine points on cross-sections of rocks, ceramics, or optical fibers.

* * * * *